United States Patent
Ruiz Ballesteros et al.

(10) Patent No.: US 11,235,081 B2
(45) Date of Patent: Feb. 1, 2022

(54) VOLATILE SUBSTANCE EVAPORATION DEVICE

(71) Applicant: Zobele Holding S.P.A., Trento (IT)

(72) Inventors: Julio César Ruiz Ballesteros, Barcelona (ES); Cedric Morhain, Barcelona (ES); Moisés Caballero Tapia, Barcelona (ES)

(73) Assignee: ZOBELE HOLDING S.P.A.

( * ) Notice: Subject to any disclaimer, the term of this patent is extended or adjusted under 35 U.S.C. 154(b) by 177 days.

(21) Appl. No.: 16/468,826

(22) PCT Filed: Dec. 13, 2017

(86) PCT No.: PCT/EP2017/082572
§ 371 (c)(1),
(2) Date: Jun. 12, 2019

(87) PCT Pub. No.: WO2018/108985
PCT Pub. Date: Jun. 21, 2018

(65) Prior Publication Data
US 2020/0069831 A1   Mar. 5, 2020

(30) Foreign Application Priority Data

Dec. 13, 2016 (ES) ............... ES201631580

(51) Int. Cl.
*A61L 9/04* (2006.01)
*A01M 1/20* (2006.01)
(Continued)

(52) U.S. Cl.
CPC ........... *A61L 9/042* (2013.01); *A01M 1/2044* (2013.01); *A61L 9/04* (2013.01); *A61L 9/12* (2013.01);
(Continued)

(58) Field of Classification Search
CPC ... A61L 9/04; A61L 9/12; A61L 9/042; A61L 2209/131; A01M 1/2044; B05B 12/08
(Continued)

(56) References Cited

U.S. PATENT DOCUMENTS 3,169,705 A * 2/1965 Geiger .................. A61L 9/14
239/43
7,481,380 B2 * 1/2009 Kvietok ............. A01M 1/2044
239/43

(Continued)

FOREIGN PATENT DOCUMENTS

| EP | 2009/003947 A2 | 1/2009 |
| EP | 2009/003947 A3 | 1/2009 |
| EP | 2050337 | 4/2009 |

OTHER PUBLICATIONS

International Search Report dated Mar. 28, 2018 from co-pending International Application No. PCT/EP2017/082572.

*Primary Examiner* — Steven J Ganey
(74) *Attorney, Agent, or Firm* — Sandberg Phoenix and von Gontard

(57) ABSTRACT

A volatile substance evaporation device includes a constant evaporation chamber (2) housing a liquid with volatile substances, an enhanced evaporation chamber (3) and an evaporation membrane (5) through which the volatile substances evaporate. The enhanced evaporation chamber (3) includes an absorbent body (6) therein. The inclusion of the absorbent body (6) enhances the evaporation rate in a simple manner and allows the enhanced evaporation to be substantially constant.

16 Claims, 2 Drawing Sheets

(51) Int. Cl.
*A61L 9/12* (2006.01)
*B05B 12/08* (2006.01)
(52) U.S. Cl.
CPC ......... *B05B 12/08* (2013.01); *A61L 2209/131* (2013.01)
(58) Field of Classification Search
USPC ............................ 239/34, 36, 39, 42, 43, 71
See application file for complete search history.

(56) References Cited

U.S. PATENT DOCUMENTS

| | | | |
|---|---|---|---|
| 2007/0057086 A1* | 3/2007 | Van Kippersluis | A61L 9/127 239/43 |
| 2007/0176015 A1* | 8/2007 | Farrell | A61L 9/127 239/34 |
| 2008/0191050 A1* | 8/2008 | Blondeau | A61L 9/12 239/71 |

* cited by examiner

VOLATILE SUBSTANCE EVAPORATION DEVICE

CROSS REFERENCE TO RELATED APPLICATION

This application is a U.S. national stage application filed under 35 U.S.C. § 371 of International Patent Application No. PCT/EP2017/082572 filed on Dec. 13, 2017, which international application claims priority to Spanish national patent application No. P201631580 filed on Dec. 13, 2016. The entirety of the foregoing applications are incorporated by reference herein.

STATEMENT REGARDING FEDERALLY SPONSORED RESEARCH OR DEVELOPMENT

Not applicable.

SEQUENCE LISTING, TABLE OR COMPUTER PROGRAM ON COMPACT DISC

Not applicable.

FIELD OF INVENTION

The present invention relates to a volatile substance evaporation device which comprises an evaporation membrane and allows increasing the evaporation rate of volatile substances.

BACKGROUND OF THE INVENTION

The use of volatile substance (fragrance or pesticide) evaporation devices, in which the volatile substances evaporate from an evaporation membrane impregnated with a liquid containing said volatile substances, is known.

Evaporation devices of this type are also known to comprise two receptacles, each provided with an evaporation membrane, where the liquid can move from a first receptacle to a second receptacle to also impregnate the membrane of the second receptacle to enhance evaporation.

However, those evaporation devices known today which comprise only one membrane have no enhancement effect whatsoever for increasing the evaporation rate, and those which comprise two receptacles and membranes are complex and do not allow the user to know how long the enhancement effect will last. Furthermore, in these known devices the enhancement effect is degressive.

An objective of the present invention is therefore to provide a volatile substance evaporation device which is simple, allows promoting evaporation, and it furthermore allows the user to know how long the enhancement effect will last and that this enhancement effect is constant.

SUMMARY OF THE INVENTION

The aforementioned drawbacks are solved by the volatile substance evaporation device, which has other advantages that will be described below.

The volatile substance evaporation device according to the present invention comprises a constant evaporation chamber housing a liquid with volatile substances, an enhanced evaporation chamber and an evaporation membrane through which the volatile substances evaporate, characterized in that said enhanced evaporation chamber comprises an absorbent body therein.

Said constant evaporation chamber is advantageously communicated with said enhanced evaporation chamber, for example, by means of a portion having a reduced section.

Furthermore, the volatile substance evaporation device according to the present invention advantageously comprises a single evaporation membrane for the constant evaporation chamber and for the enhanced evaporation chamber.

Said absorbent body is preferably in contact with the evaporation membrane.

According to a preferred embodiment, said constant evaporation chamber comprises a thicker part and a thinner part, and furthermore said thicker part of the constant evaporation chamber is closer to the portion having a reduced section than the thinner part thereof.

Said absorbent body advantageously changes its appearance throughout evaporation, such that the user can know how long the evaporation-promoting effect will last.

At least the following advantages are achieved with the volatile substance evaporation device according to the present invention:
- the evaporation rate is readily increased as a result of the presence of the absorbent body;
- it allows the enhanced evaporation to be substantially constant;
- it allows the user to know if the enhanced evaporation is active by observing whether or not the absorbent body is impregnated, as will be explained in detail below;
- it allows activating the enhanced evaporation many times in a very simple manner, for example, by simply turning the device over.

BRIEF DESCRIPTION OF THE DRAWINGS

To better understand what has been set forth, drawings schematically depicting a practical embodiment only by way of non-limiting example are attached.

DETAILED DESCRIPTION

Figure 1:
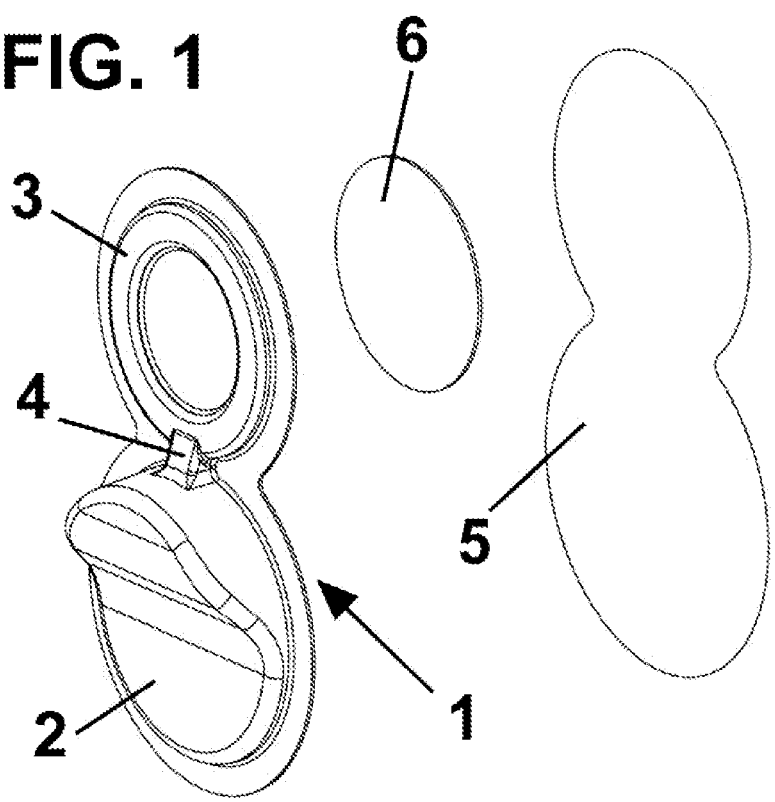
FIG. 1 is an exploded perspective view of the volatile substance evaporation device according to the present invention.
Figure 2:
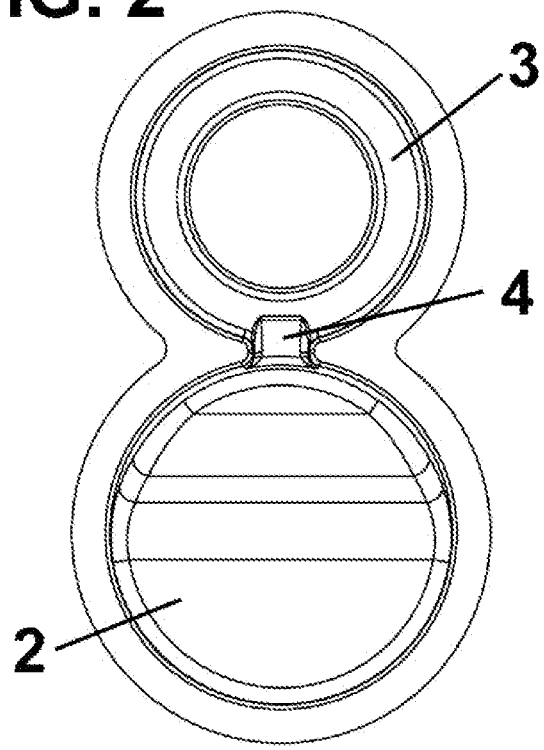
FIG. 2 is a front view of the volatile substance evaporation device according to the present invention.

The evaporation device depicted in the drawings according to the present invention comprises a casing 1 provided with two chambers: a constant evaporation chamber 2 and an enhanced evaporation chamber 3, both closed by a single evaporation membrane 5 welded to the casing 1. The constant evaporation chamber 2 houses therein a liquid with volatile substances which impregnates the evaporation membrane 5.

Before the first use, said evaporation membrane 5 is covered in a leak-tight manner by means of a sheet (not depicted in the drawings), which is removed before the first use to prevent evaporation of the volatile substances during storage.

In the depicted embodiment, the device is designed to be hung, and in this case, the constant evaporation chamber 2 is arranged in the lower part and the enhanced evaporation chamber 3 is arranged in the upper part.

Both chambers 2, 3 are preferably made as a single part and are connected to one another by a portion 4 having a reduced section.

The enhanced evaporation chamber 3 has a specific area for holding therein an absorbent body 6 made of any suitable absorbent material, and a design such that constant impregnation during evaporation is assured when the absorbent body 6 pushes against the evaporation membrane 5.

The enhancement effect will preferably be activated by turning the device over, such that the liquid inside the constant evaporation chamber 2 will go to the enhanced chamber 3 through the portion 4, impregnating the absorbent body 6. The excess liquid will return to the constant evaporation chamber 2 and the liquid in chamber 3 will evaporate through the evaporation membrane 5 in contact with the absorbent body 6. Therefore, the enhancement effect will be noticeable because the amount of evaporation surface of the membrane 5 increases.

The user will be able to know at all times when the enhancement effect of the device has come to an end, since the absorbent body 6 impregnated with a liquid will change its appearance upon activation, for example, changing its color or intensity, regaining its original appearance once the liquid has evaporated. There are several ways to do this, with two possibilities explained below.

The first possibility consists of using a polyethylene-based microporous film as an absorbent body 6 which loses its appearance upon impregnation, becoming completely transparent, and as the impregnation of said film fades away it recovers the original appearance and becomes opaque.

A second embodiment is to use a substrate of cellulose origin with a print containing a message or image as an absorbent body 6. Upon impregnation, the liquid would not allow seeing the print, but as the impregnation of the substrate fades away, the print would become visible again, informing the user that the enhancement effect has come to an end.

An additional advantage is that the amount of liquid in the enhanced evaporation chamber 3 is always the same regardless of the amount of liquid remaining in the constant evaporation chamber 2.

If desired, and as depicted in the drawings, the constant evaporation chamber 2 can have a design that is thicker in one part than in another, specifically thicker in the part close to the portion 4 connecting both chambers 2, 3, to assure that the evaporation surface of the membrane 5 does not significantly decrease over time, since it is known that the membrane 5 evaporates better in the area which is in contact with the liquid.

It must be indicated that the device can have any shape, for example, a cylindrical, square or rhomboid shape.

Although reference has been made to a specific embodiment of the invention, it is obvious for a person skilled in the art that the volatile substance evaporation device described is susceptible to a number of variations and modifications, and that all the mentioned details can be replaced with other technically equivalent details without departing from the scope of protection defined by the attached claims.

What is claimed is:

1. A volatile substance evaporation device comprising:
    a first chamber housing a liquid with volatile substances;
    a second chamber;
    an evaporation membrane through which the volatile substances evaporate, the evaporation membrane closing over both the first chamber and the second chamber and enabling the liquid with volatile substances to evaporate from the first chamber through the evaporation membrane and from the second chamber through the evaporation membrane; and
    the second chamber comprising an absorbent body therein.

2. The volatile substance evaporation device according to claim 1, wherein said first chamber communicates with said second chamber.

3. The volatile substance evaporation device according to claim 2, wherein said first chamber communicates with said second chamber through a portion of the device having a cross section area that is smaller than a cross section area of the first chamber and is smaller than a cross section area of the second chamber.

4. The volatile substance evaporation device according to claim 3, wherein said first chamber comprises a first part having a first cross section area and a second part having a second cross section area, the first cross section area being larger than the second cross section area; and
    said first part of the first chamber is closer to the portion of the device than the second part thereof.

5. The volatile substance evaporation device according to claim 4, wherein said absorbent body changes its appearance throughout evaporation.

6. The volatile substance evaporation device according to claim 2, wherein said absorbent body changes its appearance throughout evaporation.

7. The volatile substance evaporation device according to claim 3, wherein said absorbent body changes its appearance throughout of operation.

8. The volatile substance evaporation device according to claim 1, wherein the evaporation membrane is a single membrane that extends over and closes the first chamber and the second chamber.

9. The volatile substance evaporation device according to claim 8, wherein said absorbent body changes its appearance throughout evaporation.

10. The volatile substance evaporation device according to claim 1, wherein said absorbent body is in contact with the evaporation membrane.

11. The volatile substance evaporation device according to claim 10, wherein said absorbent body changes its appearance throughout evaporation.

12. The volatile substance evaporation device according to claim 1, wherein said first chamber comprises a first part having a first cross section area and a second part having a second cross section area, the first cross section area being larger than the second cross section area.

13. The volatile substance evaporation device according to claim 12, wherein said first part of the first chamber is closer to the portion of the device than the second part of the first chamber.

14. The volatile substance evaporation device according to claim 13, wherein said absorbent body changes its appearance throughout of operation.

15. The volatile substance evaporation device according to claim 12, wherein said absorbent body changes its appearance throughout of evaporation.

16. The volatile substance evaporation device according to claim 1, wherein said absorbent body changes its appearance throughout evaporation.

* * * * *